United States Patent [19]

Albu et al.

[11] Patent Number: 5,866,819
[45] Date of Patent: Feb. 2, 1999

[54] ULTRASONIC THICKNESS MEASUREMENT OF MULTILAYER STRUCTURES

[75] Inventors: Dan Albu; Salem M. Taboun, both of Windsor, Canada

[73] Assignee: Walbro Corporation, Cass City, Mich.

[21] Appl. No.: 910,124

[22] Filed: Aug. 13, 1997

[51] Int. Cl.[6] .......................... G01N 29/06; G01N 29/10
[52] U.S. Cl. ............................................................. 73/629
[58] Field of Search ............................ 73/597, 602, 620, 73/609–616, 629, 627, 644

[56] References Cited

U.S. PATENT DOCUMENTS

| | | | |
|---|---|---|---|
| 3,934,458 | 1/1976 | Beretsky et al. | |
| 4,167,880 | 9/1979 | George | 73/644 |
| 4,738,139 | 4/1988 | Blessing et al. | 73/644 |
| 5,001,932 | 3/1991 | Light et al. | 73/644 |
| 5,038,615 | 8/1991 | Trulson et al. | 73/597 |
| 5,167,157 | 12/1992 | Wertz et al. | 73/627 |
| 5,271,274 | 12/1993 | Ichuri-Yakub et al. | 73/597 |
| 5,608,165 | 3/1997 | Mozurkewich, Jr. | 73/599 |

*Primary Examiner*—Michael Brock
*Assistant Examiner*—Rose M. Miller
*Attorney, Agent, or Firm*—Barnes, Kisselle, Raisch, Choate, Whittemore & Hulbert,P.C.

[57] ABSTRACT

A non-destructive method and apparatus for determining the thickness of individual layers of different materials in a multilayer structure particularly useful in analyzing the layers in a multilayer plastic fuel tank, utilizes a constant and relatively high frequency ultrasonic pulse transmitted into the multilayer structure and records the time when interference pulses are received to determine the thickness of the individual layers in the multilayer structure. The interference pulses are generated at the interface between adjacent layers of sufficiently different materials and thus, the time between interference pulses is a function of the amount of time needed for the ultrasonic pulse to pass through a layer of material. The duration between reflected pulses is called the transmission time which is the time for the ultrasonic frequency to originally pass through the material and also the time for the reflected pulse to bounce back to the transducer and is thus equal to twice the time needed for the ultrasonic pulse to pass through the layer. Therefore, the thickness of a layer within a multilayer structure can be readily computed as one-half of the transmission time multiplied by the speed of sound through the material comprising that layer.

32 Claims, 2 Drawing Sheets

ULTRASONIC THICKNESS MEASUREMENT OF MULTILAYER STRUCTURES

FIELD OF THE INVENTION

This invention relates generally to ultrasonic measuring and more particularly to an ultrasonic method and apparatus for measuring the thickness of individual layers of different materials of a multilayer structure.

BACKGROUND OF THE INVENTION

Environmental concerns and regulations have spurred the need to reduce the amount of hazardous hydrocarbon vapors emitted by vehicles and have led to the development of new technologies for manufacturing plastic fuel tanks. A fuel tank constructed from a single layer of a plastic, such as high density polyethylene, has been found to have an unacceptably high permeation rate of fuel vapor therethrough. Therefore, current plastic fuel tanks are formed with multiple layers one of which is a vapor barrier layer and these tanks have reduced the amount of hydrocarbons released into the atmosphere by as much as 60 times over single layer untreated plastic fuel tanks.

A typical multilayer plastic fuel tank construction comprises an outer layer of high density polyethylene, an inner layer of high density polyethylene, and a vapor barrier layer disposed between them. The vapor barrier layer is typically a polymer such as ethylene vinyl alcohol which requires an adhesive layer adjacent both the outer and inner layers to join the high density polyethylene with the ethylene vinyl alcohol. A multilayer plastic fuel tank is more difficult to manufacture than a single layer plastic fuel tank. In mass production, to insure the quality of multilayer fuel tanks and the vapor barrier, it is important to determine the thickness of the individual layers of the multilayer structure and in particular the adhesive and barrier layers both from one tank to the next and at various locations within an individual tank. The most critical and difficult areas to measure tend to be at the corners, edges and other areas of the tank where the contour of the multilayer wall changes rapidly.

Previously, testing and sampling of manufactured plastic fuel tanks required cutting a cross section from various portions of the fuel tanks and preparing each cross section to be visually inspected under a microscope to measure the thickness of the various layers. This is undesirable because of the time required to prepare and inspect the sample cross sections of the fuel tank and also because of the destruction of the fuel tank as well as the scrap and waste created when conducting such a test.

U.S. Pat. No. 5,608,165 discloses a non-destructive method for determining the thickness of a barrier layer in a multilayer plastic fuel tank which utilizes an interference technique with a varying frequency and relatively low frequency and continuous ultrasonic signal to determine a frequency which produces an attenuated signal which can thereby be used to determine the thickness of only the vapor barrier.

SUMMARY OF THE INVENTION

A non-destructive method and apparatus for determining the thickness of individual layers of different materials in a multilayer structure and particularly a multilayer plastic fuel tank, utilizes a constant frequency and relatively high frequency ultrasonic pulse transmitted into the multilayer structure and records the times when echoes are received to determine the thickness of the individual layers in the multilayer structure. An echo pulse is generated at the interface between adjacent layers of materials having a sufficiently different density or index of refraction and thus, the time between transmitted and echo pulses is a function of the amount of time needed for the ultrasonic pulse to pass through a layer of material. The duration between transmitted and reflected pulses is called the transmission time which is the time for the ultrasonic frequency transmitted pulse to originally pass through the material and also the time for the reflected pulse to bounce back to the transducer and is thus equal to twice the time needed for the ultrasonic pulse to pass through the layer. Therefore, the thickness of a layer within a multilayer structure can be readily computed as one-half of the transmission time multiplied by the speed of sound through the material comprising that layer.

Either immersion or preferably contact type transducers may be used with the present invention to transmit the ultrasonic pulse which is generated and conveyed to the transducer by a pulse source. The transducer also senses the reflected pulses and relays them to a pulse receiver which may display the pulses as a function of transmission time for manual calculation of the layer thickness. Preferably, an analog-to-digital converter is coupled with the pulse receiver to digitize the data from the reflected pulses received so that they may be analyzed by a microprocessor which performs the thickness calculations automatically. More preferably, the microprocessor is a personal computer and the pulse source, pulse receiver and analog-to-digital converter are hardware components of the personal computer enabling fast, easy, reliable and efficient analyzing of the results.

Thus, the present invention provides a non-destructive method and apparatus for determining the thickness of individual layers in a multilayer structure such as a plastic fuel tank, to ensure the quality of the fuel tanks throughout a production run of tanks. Further, the data gathered during the ultrasonic testing can be either manually analyzed or automatically analyzed by a personal computer thereby greatly reducing the time needed to conduct the test.

Objects, features and advantages of this invention include providing a method and apparatus for determining the thickness of individual layers of a multilayer structure that does not require destruction of the fuel tanks tested, can determine the thickness of individual layers of a sharply curved multilayer structure, is less time consuming than destructive testing methods, can be substantially automated and used with a personal computer, utilizes relatively high ultrasonic frequencies and a high sampling rate for increased resolution and reliability of the data obtained, can utilize commercially available hardware and software as well as commercially available transducers, utilizes a single ultrasonic frequency, can simultaneously determine the thickness of multiple layers, is not dependent on the relative thickness of adjacent layers, provides reliable data, is of relatively simple design and economical manufacture, is simple to use and provides fast and accurate data to help increase the quality of production of multilayer plastic fuel tanks.

BRIEF DESCRIPTION OF THE DRAWINGS

These and other objects, features and advantages of this invention will be apparent from the following detailed description of the preferred embodiment and best mode, appended claims and accompanying drawings in which:

DETAILED DESCRIPTION OF THE PREFERRED EMBODIMENTS

Figure 1:
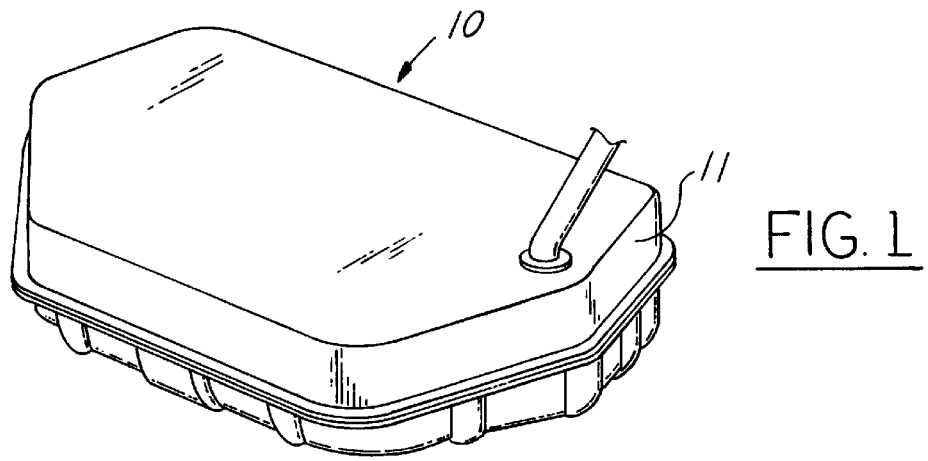
FIG. 1 is a perspective view of a molded plastic fuel tank.
Figure 2:
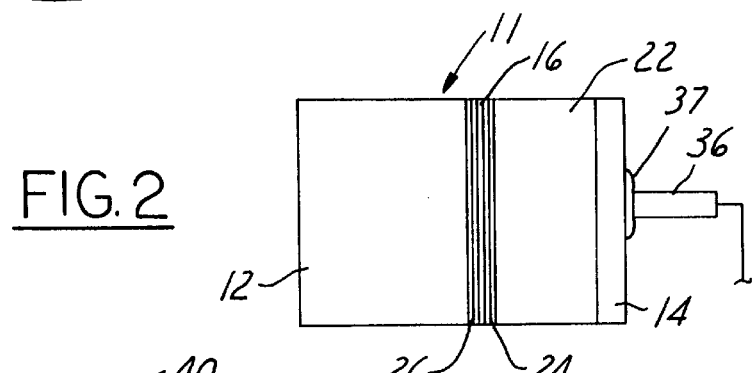
FIG. 2 is a fragmentary sectional view of a multilayer plastic fuel tank wall.

Referring in more detail to the drawings, FIG. 1 shows a multilayer molded plastic fuel tank 10 as is commonly used, for example, in the automotive industry. As shown in FIG. 2, the walls 11 of the fuel tank 10 preferably have inner 12 and outer 14 layers formed primarily of polyethylene and an intermediate vapor barrier layer 16 formed of a copolymer such as ethylene vinyl alcohol to reduce the permeation of fuel vapor through the fuel tank 10. The tank walls 11 may be formed by coextruding the various layers of different materials. The plastic fuel tanks 10 are particularly desirable because of their light weight, resistance to corrosion and ease of manufacturing.

As shown in FIG. 2, the fuel tank 10 has multiple layers including: an outer layer 14 of high density polyethylene (HDPE) which may also have some carbon black or poly black mixed therein to provide coloration; a re-grind layer 22 of HDPE which is composed of re-ground scrap materials from the manufacturing of the fuel tanks 10 and/or salvaged and re-ground HDPE; an outer adhesive layer 24; the vapor barrier layer 16; an inner adhesive layer 26; and an inner layer 12 of virgin high density polyethylene. The vapor barrier layer 16 is preferably ethylene vinyl alcohol (EVOH) and the adhesive layers may be of a wide variety of materials with one current example sold under the trade name ADMER by Evalca, Inc. The inner and outer adhesive layers 24, 26 are necessary to attach the adjacent layers of HDPE to the vapor barrier layer 16 and thereby increase the structural integrity of the fuel tank 10 which is paramount for passing various crush resistance specifications in the automotive industry. The vapor barrier layer 16 is necessary to reduce the amount of hydrocarbon vapors which would diffuse or escape through the fuel tank walls 11 which are composed primarily of HDPE. The outer layer 14 and re-grind layer 22 are of substantially the same composition such that they cannot be differentiated with ultrasonic measurements.

A typical multilayer plastic fuel tank wall 11 has a thickness of between about 2.5 mm and 8 mm, with an optimal total wall thickness of about 5 mm. Nominal values for the individual layers of the multilayer plastic fuel tank 10 are as follows: the outer layer 14 plus the re-grind layer 22 comprise between about 40 to 50 percent of the total wall thickness; the outer adhesive layer 24 comprises between about 1 to 4 percent of the total wall thickness; the vapor barrier layer 16 comprises between about 2 to 5 percent of the total wall thickness; the inner adhesive layer 26 comprises between about 1 to 4 percent of the total wall thickness; and the inner layer 12 comprises between about 40 and 50 percent of the total wall thickness. These ranges of the thickness of the individual layers are illustrative only, and can be readily varied during the coextrusion of the fuel tank walls 11 during the manufacture of the fuel tanks 10.

Throughout a production run of fuel tanks 10, the thickness of the individual layers must be controlled to assure optimum performance and quality of the fuel tank 10 in use. The thickness of the inner 12 and outer 14 layers of polyethylene is important because these layers provide structural protection of the vapor barrier layer 16 and also the structural integrity of the fuel tank 10 itself. The thickness of the adhesive layers 24, 26 is important to insure adequate attachment between the adjacent layers of HDPE and the vapor barrier layer 16. Finally, the thickness of the vapor barrier layer 16 is important to prohibit the permeation of the hydrocarbon vapors through the fuel tank 10 and into the atmosphere.

Figure 3:
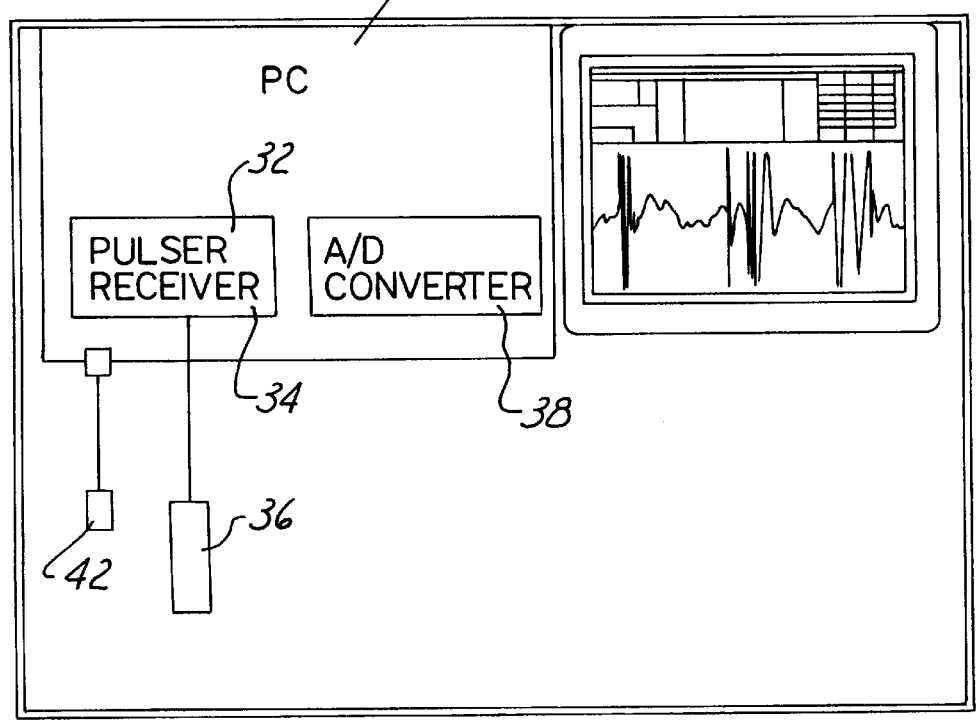
FIG. 3 is a schematic view illustrating an apparatus for automatically processing the thickness of individual layers of the multilayer structure according to this invention.

Referring to FIG. 3, an apparatus 30 is shown which utilizes an ultrasonic method to determine the thickness of the individual layers of the multilayer plastic fuel tank 10. The apparatus 30 has a pulse source 32, a pulse receiver 34 and an ultrasonic transducer 36 coupled to the pulse source 32 and to the pulse receiver 34. The pulse source 32 produces an electrical signal which intermittently vibrates the transducer 36 at a known constant frequency to send an ultrasonic pulse into the multilayer plastic fuel tank 10 whereupon echoes, or reflected pulses are generated at the interfaces of different layers within the fuel tank 10. The reflected pulses are returned to the transducer 36 and vibrate it whereupon these vibrations are communicated to the pulse receiver 34 as electrical pulses which are recorded and which enable the determination of the thickness of the individual layers of the fuel tank 10. Preferably, an analog-to-digital converter 38 is coupled with the pulse receiver 34 to convert the pulses received into digital form whereby they may be automatically processed by a microprocessor such as a personal computer 40. More preferably, the pulse source 32, pulse receiver 34 and analog-to-digital converter 38 are all commercially available hardware components for a personal computer 40 which may be readily connected to the computer 40. Also preferably, the personal computer 40 may be adapted with software capable of interpreting the recorded data from the ultrasonic transmissions to automatically interpret the received data into the thicknesses of the various layers. Current hardware components which have been used include a combination pulse source 32 and pulse receiver 34 sold under the name Matec SR9000 series and an STR8100 series analog-to-digital converter 38 both of which are ISA cards and can be installed as part of the personal computer 40 configuration. The ISA cards are commercially available from Matec Instruments, Inc. of 56 Hudson Street, Northborough, Mass. 01532, USA.

Figure 5:
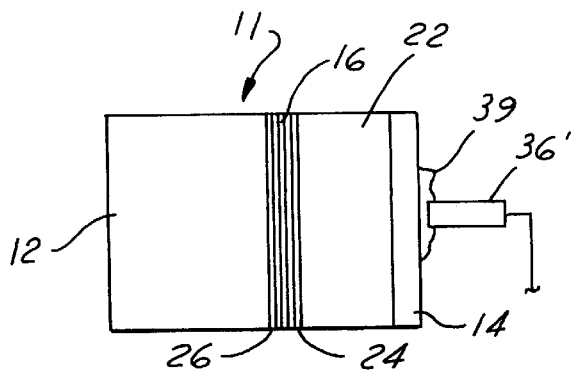
FIG. 5 is a fragmentary sectional view of a multilayer plastic fuel tank wall and an immersion type transducer adjacent to the wall.

The transducer 36 is preferably of the contact type which directly contacts the outer surface of the fuel tank 10. A liquid medium such as water 37 is necessary with the contact type transducer to remove any air from the interface between the transducer transmission face and the fuel tank surface. However, as shown in FIG. 5, the transducer 36 may be of the immersion type which transmits the ultrasonic pulse through a liquid coupling medium such as oil 39 and focuses it through a lens onto the tank wall 11 without physically bearing on the tank. With an immersion transducer the ultrasonic pulse is usually focused onto the tank wall by varying the distance between them. The contact type transducer is preferred because it provides much better resolution when measuring curved surfaces, such as a curve adjacent the corners and edges of the fuel tank, and it eliminates the need to focus the transducer which would be required with an immersion type transducer. A suitable contact transducer 36 is commercially available from Technisonic Research, Inc., 777 Commerce Drive, Fairfield, Conn. 06432, USA.

Transducers 36 operating at different constant frequencies may be utilized to provide a signal with a resolution optimized for the particular multilayer structure being measured. Empirical data has shown that for a typical plastic fuel tank 10 having individual layers of the materials and thicknesses as previously described and a total thickness of about 5 mm, the optimal frequency is about 15 MHz. With this frequency, a strong resolution of the signal is obtained which provides a good definition of each of the individual layers as well as the total wall 11 thickness. In general, the higher the frequency the greater the resolution of the signal, however, higher frequencies are more quickly attenuated in HDPE than are low frequencies. This greatly limits the use of higher frequencies with an optimal frequency range determined through experimentation to be between about 10 MHz to 20 MHz. Further, to more accurately record the results, the pulse receiver 34 preferably has a high sampling rate which is preferably on the order of about 100 MHz. This will obtain a multitude of data points which will provide an accurate plot of the reflected pulses over time.

Figure 4:
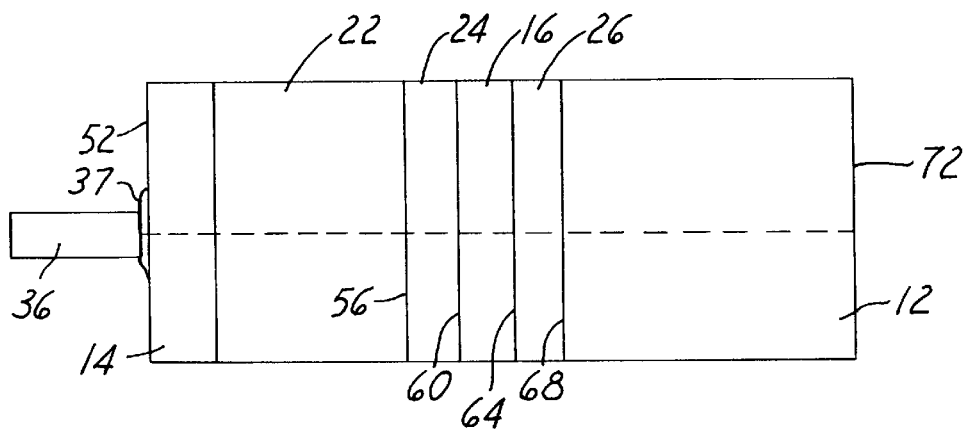
FIG. 4 is plot of an ultrasonic echo or reflected pulses obtained according to this invention.
Figure 4:
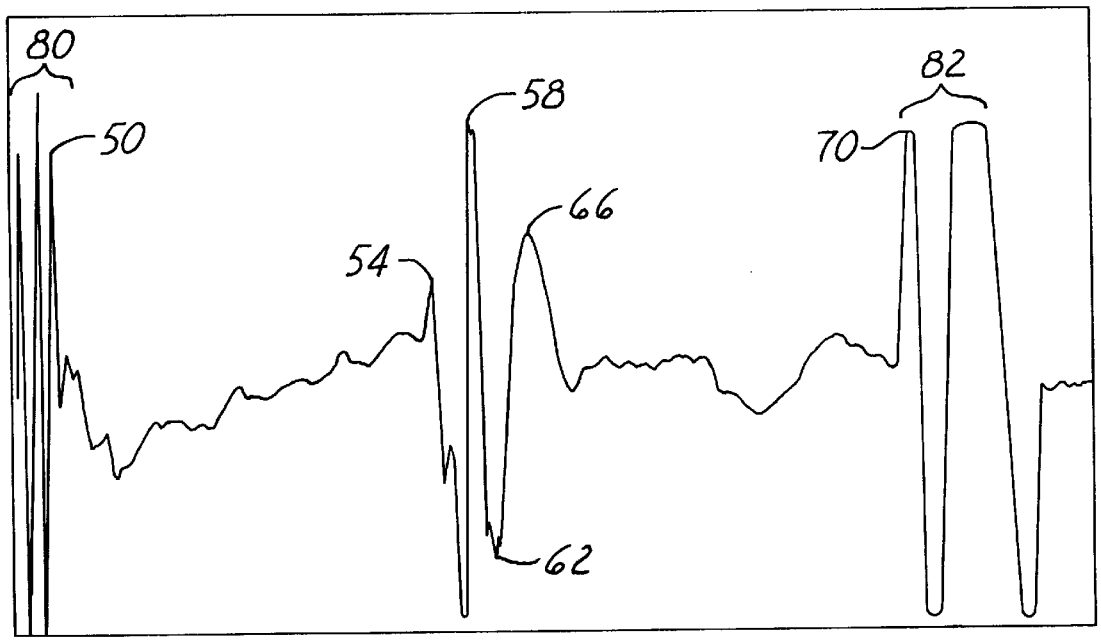

In use, the user places the transducer 36 on the desired portion of the fuel tank 10 to be measured whereupon the pulse source 32 generates an electrical signal which vibrates the transducer 36 at the desired frequency. The user freezes the signal by triggering a switch 42 (such as a computer mouse) attached to the personal computer 40, and a short ultrasonic pulse is generated in the transducer 36 and transferred into the wall 11 of the plastic fuel tank 10. As the ultrasonic pulse travels through the multilayer wall 11 structure, there are reflections at each interface between materials which are of a different density or index of refraction. These reflections or reflected pulses are returned to the transducer 36 where they are recorded by the pulse receiver 34 as a function of the time received. As shown in FIG. 4, a plot can be produced of the reflected pulses over time which can be manually analyzed to determine the thickness of the individual layers and the total thickness of the fuel tank wall 11. Preferably, a computer software program analyzes the recorded data and automatically interprets the data into the corresponding thickness of the individual layers.

Empirically, the various peaks as shown in the plot of FIG. 4 can be correlated to the interfaces of the various layers in the fuel tank 10. For example, a first peak 50 represents the outer surface 52 of the fuel tank 10. A second peak 54 represents the interface 56 between the re-grind layer 22 and the outer adhesive layer 24 (as discussed previously, the interface between the outer layer 14 of polyethylene and the re-grind layer 22 is not determinable by ultrasonic measurement). A third peak 58 represents the interface 60 between the outer adhesive layer 24 and the vapor barrier layer 16. A fourth peak 62 represents the interface 64 between the vapor barrier layer 16 and the inner adhesive layer 26. A fifth peak 66 represents the interface 68 between the inner adhesive layer 26 and the inner layer 12 of polyethylene. Finally, a sixth peak 70 represents the inner surface 72 of the fuel tank wall 11.

The time between the various peaks represents the transmission time of the ultrasonic signal through the corresponding layer of material. The transmission time is the time for: (1) the generated ultrasonic pulse to travel through the layer; and (2) the time for the reflected pulse to travel back through that layer of material. Thus, the transmission time is equal to twice the time needed for an ultrasonic pulse of the given frequency to travel through the corresponding layer of material. Therefore, the thickness of an individual layer in the multilayer plastic fuel tank 10 can be calculated by multiplying one-half of the transmission time and the average speed of sound in that material. This computation can be easily done either manually or automatically by a microprocessor such as that in the personal computer 40. In a similar manner the total thickness of the entire wall 11 can be calculated.

Preferably, the speed of sound in each material is empirically determined by utilizing the apparatus 30 itself and calibrating it by using a separate sample of known thickness of each material for each layer of the wall. However, if desired standard published values of the speed of sound in each material may be utilized and entered into the computer program for calculating the thickness of each layer of material.

It has been empirically determined that with a multilayer wall, such as the tank wall 11, the beginning or exterior surface 52 in contact with the transducer 30 is always characterized by a three peak wave form 80, as shown in FIG. 4, with the third peak 50 representing the exterior surface 52 and the last or innermost surface of the wall is always characterized by a two peak wave form 82 with the first peak 70 representing the innermost surface 72 which is the interface between HDPE material 12 and the atmospheric air within the empty fuel tank. Moving inward from both ends, the peak of the highest amplitude 58 represents the interface 60 between the outer adhesive layer 24 and the vapor barrier layer 16. Moving outwardly in both directions from this peak 58, the next peaks of significant magnitude 54 and 62, correspond to the interfaces 56 and 64, respectively. As shown, the peak 62 has a negative magnitude due to the change in material at the interface 64 from the material of layer 16 with a higher speed of sound to the material of layer 26 with a lower speed of sound. Finally, the interface 68, which represents the interface between the inner adhesive layer 26 and the inner HDPE layer 12, is located by selecting the next peak of significant magnitude 66 between the peaks 62 and 70.

This distinctive wave form enables automated computer analysis utilizing appropriate software to determine each peak 50, 54, 58, 66 and 70 and the valley or peak of negative magnitude 62 of interest and calculations determining the actual thickness of each layer of material 22, 24, 16, 26 and 12 of the multilayer wall 11. This recognition of the wave form and calculation of the thickness of each layer may be done by using a program developed by Lab View software and a suitable personal computer. This Lab View software is commercially available from National Instruments Company of 6504 Bridge Point Parkway, Austin, Tex. 78730-5039.

Thus, the apparatus 30 uses a simple method utilizing an ultrasonic signal to determine the thickness of the individual layers of the multilayer structure such as a multilayer plastic fuel tank 10. The signal utilized is at a constant and relatively high frequency providing data with a high resolution and accuracy. The method and apparatus 30 utilize commercially available components and can be readily adapted for use with a personal computer 40 to automatically analyze the data and compute the results. Further, this method is non-destructive and considerably less time consuming and labor intensive than previous methods and enables an increased quality control of the manufacture of the fuel tanks 10.

We claim:

1. A method of measuring the thickness of individual layers of different materials in a multilayer structure comprising the steps of:

a) transmitting an ultrasonic pulse at a substantially constant frequency of not more than 30 MHz into the multilayer structure;

b) receiving reflected pulses from the interfaces between layers of different materials of substantially different thicknesses within the multilayer structure and selecting those reflected pulses that correspond to the interface of adjacent layers based on the amplitude of the reflected pulses received;

c) determining the transmission time of the ultrasonic pulse for a layer within the multilayer structure where the transmission time of the ultrasonic pulse for a given layer begins when a reflected pulse from a first face of that layer is received and ends when a reflected pulse from a first face of the next layer is received; and d) determining the thickness of the layer as a function of the transmission time and the speed of sound in the material of the layer.

2. The method of claim 1 wherein the thickness of a layer is determined based on one-half the transmission time multiplied by the average speed of sound in the material of the layer.

3. The method of claim 1 wherein the layers to be measured in the multilayer structure are formed of a plastic material and have a different density than their adjacent layers.

4. The method of claim 1 wherein the substantially constant frequency of the ultrasonic pulse is between about 10 and 20 MHz.

5. The method of claim 1 wherein the substantially constant frequency of the ultrasonic pulse is between about 14 to 16 MHZ.

6. The method of claim 1 wherein the multilayer structure is a plastic fuel tank having at least an outer layer, an inner layer and a vapor barrier layer disposed between the outer layer and inner layer.

7. The method of claim 6 which further comprises a pair of adhesive layers with an outer adhesive layer disposed between the vapor barrier layer and the outer layer and an inner adhesive layer disposed between the vapor barrier layer and the inner layer.

8. The method of claim 7 which also comprises the step of plotting the reflected pulses over time whereby reflected pulses can be correlated to the corresponding interface between adjacent materials based on the time received and on distinguishing characteristics which remain constant among fuel tanks of similar construction.

9. The method of claim 8 wherein the interface between the outer adhesive layer and the vapor barrier layer is characterized by a single peak having the highest magnitude and located between the peaks of the outer layer and the inner layer.

10. The method of claim 9 wherein the interface between the outer adhesive layer and the outer layer and the interface between the vapor barrier layer and the inner adhesive layer are located by selecting the next peak above a threshold magnitude adjacent each side of the peak representing the interface between the outer adhesive layer and the vapor barrier layer and the peak corresponding to the vapor barrier layer and inner adhesive layer interface is a negative peak, or valley, due to the change in the speed of sound between the materials of those layers.

11. The method of claim 10 wherein the interface between the inner adhesive layer and the inner layer is located by selecting the next peak above a threshold magnitude adjacent the peak corresponding to the interface between the inner adhesive layer and the vapor barrier layer.

12. The method of claim 6 wherein the outer layer and inner layer are formed primarily of high density polyethylene and the vapor barrier layer is formed of ethylene vinyl alcohol.

13. The method of claim 6 which also comprises the step of plotting the reflected pulses over time whereby reflected pulses can be correlated to the corresponding interface between adjacent materials based on the time received and on distinguishing characteristics which remain constant among fuel tanks of similar construction.

14. The method of claim 13 wherein the plot of the reflected pulses can be interpreted automatically by a microprocessor.

15. The method of claim 13 wherein on the plot of reflected pulses the beginning of the outer layer is characterized by three closely adjacent peaks of relatively large magnitude.

16. The method of claim 13 wherein on the plot of reflected pulses the end of the inner layer is characterized by a pair of closely adjacent peaks of relatively large magnitude.

17. The method of claim 13 wherein on the plot of reflected pulses the beginning of the vapor barrier layer is characterized by a single peak of relatively large magnitude located between the reflected pulses which correspond to the inner layer and the outer layer.

18. The method of claim 6 wherein the vapor barrier layer comprises not more than about five percent of the total thickness of the plastic fuel tank.

19. The method according to claim 18 wherein the inner layer and the outer layer combined comprise at least 75 percent of the total thickness of the plastic fuel tank.

20. The method according to claim 19 wherein the total thickness of the plastic fuel tank is between 2.5 mm and 8 mm.

21. The method of claim 1 wherein the reflected pulses are sampled at a rate of about between 50 MHz to 150 MHz.

22. The method of claim 1 wherein the reflected pulses are sampled at a rate of about 100 MHz.

23. An apparatus for determining the thickness of individual layers of different materials in a multilayer structure comprising:

a pulse generator;

a pulse receiver; and an ultrasonic transducer coupled to the pulse generator and to the pulse receiver whereby the pulse generator produces an electrical signal which vibrates the transducer at a predetermined substantially constant frequency to send an ultrasonic pulse at a frequency of not more than 30 MHz into the multilayer structure whereupon reflected pulses from the interfaces of different layers of the multilayer structure are returned to the transducer and vibrate it, these vibrations are communicated to the pulse receiver and are recorded as a finction of time to enable the determination of the thickness of individual layers of the multilayer structure as a function of the time between the peak amplitude of reflected pulses selected based on the amplitude of the reflected pulses to correspond to the interface of adjacent layers of the multilayer structure and the speed of sound for the materials of the layers.

24. The apparatus of claim 23 which also comprises an analog-to-digital converter coupled to the pulse receiver to convert the pulses received by the pulse receiver into digital form and a microprocessor coupled to the converter and configured to determine the relative time of receipt of reflected pulses and to thereby determine the thickness of individual layers as a function of the speed of sound in the material of the individual layers.

25. The apparatus of claim 24 wherein the microprocessor is a computer having software capable of determining the thickness of individual layers based on the digital output of the converter.

26. The apparatus of claim 24 wherein the pulse source, pulse receiver and converter are all hardware components of the computer.

27. The apparatus of claim 24 wherein the converter has a sampling rate of between 50 MHz and 150 MHz.

28. The apparatus of claim 24 wherein the converter has a sampling rate of about 100 MHz.

29. The apparatus of claim 23 wherein the transducer is a contact type transducer and an air displacement medium is disposed between the multilayer structure and the transducer to exclude any air between them.

30. The apparatus of claim 29 wherein the air displacement medium is water.

31. The apparatus of claim 23 wherein the transducer is an immersion type transducer having a lens spaced from the structure, immersed in a bridging medium and focused by varying the distance between the lens and the structure.

32. The apparatus of claim 31 wherein the bridging medium is water.

* * * * *

UNITED STATES PATENT AND TRADEMARK OFFICE
CERTIFICATE OF CORRECTION

PATENT NO. : 5,866,819
DATED : February 2, 1999
INVENTOR(S) : Dan Albu/Salem M. Taboun It is certified that error appears in the above-identified patent and that said Letters Patent is hereby corrected as shown below:

Title page, Item [22]

Change the filing date from August 13, 1997 to "August 12, 1997".

Signed and Sealed this

Ninth Day of May, 2000

Attest:

Q. TODD DICKINSON

*Attesting Officer*      *Director of Patents and Trademarks*